United States Patent
Werner

(10) Patent No.: US 8,911,436 B2
(45) Date of Patent: Dec. 16, 2014

(54) ELECTROSURGICAL HF GENERATOR

(75) Inventor: Erich Werner, Wannweil (DE)

(73) Assignee: Erbe Elek Tromedizin GmbH, Tuebingen (DE)

( * ) Notice: Subject to any disclaimer, the term of this patent is extended or adjusted under 35 U.S.C. 154(b) by 966 days.

(21) Appl. No.: 13/060,963

(22) PCT Filed: Aug. 14, 2009

(86) PCT No.: PCT/EP2009/005916
§ 371 (c)(1),
(2), (4) Date: Feb. 25, 2011

(87) PCT Pub. No.: WO2010/025818
PCT Pub. Date: Mar. 11, 2010

(65) Prior Publication Data
US 2011/0160718 A1    Jun. 30, 2011

(30) Foreign Application Priority Data
Aug. 27, 2008   (DE) .......................... 10 2008 039 884

(51) Int. Cl.
*A61B 18/12* (2006.01)
*A61B 18/00* (2006.01)

(52) U.S. Cl.
CPC .............. *A61B 18/12* (2013.01); *A61B 18/1206* (2013.01); *A61B 18/1233* (2013.01); *A61B 2018/00875* (2013.01); *A61B 2018/0066* (2013.01)
USPC .............................................. 606/34; 606/37

(58) Field of Classification Search
CPC ............... A61B 18/12; A61B 18/1206; A61B 2018/00875; A61B 2018/0066; A61B 18/1233
USPC ..................................... 606/34, 37
See application file for complete search history.

(56) References Cited

U.S. PATENT DOCUMENTS

| | | | | |
|---|---|---|---|---|
| 4,306,200 A | * | 12/1981 | Takayama ...................... | 330/277 |
| 4,571,560 A | * | 2/1986 | Dobrovolny ................... | 333/174 |
| 5,647,869 A | * | 7/1997 | Goble et al. ..................... | 606/37 |
| 6,074,386 A | * | 6/2000 | Goble et al. ..................... | 606/34 |
| 2007/0118102 A1 | * | 5/2007 | Mihori ............................ | 606/32 |
| 2007/0173810 A1 | * | 7/2007 | Orszulak ......................... | 606/37 |
| 2010/0198213 A1 | * | 8/2010 | Lario Garcia et al. .......... | 606/33 |
| 2011/0172656 A1 | * | 7/2011 | Schall et al. .................... | 606/34 |
| 2013/0345689 A1 | * | 12/2013 | Ruddenklau et al. ........... | 606/33 |
| 2014/0018795 A1 | * | 1/2014 | Shilev et al. .................... | 606/41 |

FOREIGN PATENT DOCUMENTS

| | | |
|---|---|---|
| DE | 39 04 558 A1 | 8/1990 |
| DE | 100 46 592 A1 | 4/2002 |
| DE | 695 34 881 T2 | 9/2006 |
| EP | 1 532 952 A1 | 5/2005 |
| EP | 1 693 015 A2 | 8/2006 |
| EP | 1 810 629 A2 | 7/2007 |
| EP | 1 836 985 A2 | 9/2007 |
| GB | 2 214 430 A | 9/1989 |
| JP | 8-56955 | 3/1996 |
| WO | WO 2004/062516 A1 | 7/2004 |

* cited by examiner

*Primary Examiner* — Linda Dvorak
*Assistant Examiner* — Jocelyn D Ram
(74) *Attorney, Agent, or Firm* — Dickstein Shapiro LLP

(57) ABSTRACT

An electrosurgical high frequency (HF) generator for cutting and/or coagulating biological tissue. The generator comprises a power supply and a generator stage for exciting an HF oscillation signal in an output filter comprising a parallel resonant circuit coupled to a series resonant circuit, to which at least one electrode is connected. The generator has an improved efficiency level if the series resonant circuit has a resonance frequency that is higher than the resonance frequency of the parallel resonant circuit.

15 Claims, 2 Drawing Sheets

ELECTROSURGICAL HF GENERATOR

FIELD OF THE INVENTION

The invention relates to an electrosurgical high frequency (HF) generator, for cutting and/or coagulating biological tissue, having an improved efficiency level.

BACKGROUND

Electrosurgical HF generators are often used to cut or coagulate biological tissue in modern surgery. For this purpose, an HF signal with a frequency greater than 300 kHz is produced by an electrosurgical HF generator and is applied, via an electrode, by a surgeon at the site to be treated. Electrosurgical HF generators comprise a power supply for supplying a generator stage that excites an HF oscillation in an output filter, which comprises a parallel resonant circuit and a series resonant circuit. An electrosurgical HF generator of this type is known, for example, from DE 39 04 558 A1.

A problem in the development of electrosurgical HF generators is that they have to have a very high level of efficiency. Otherwise, a cooling system, which would not be acceptable in operating theatres, would be needed for the electrosurgical HF generator; in addition, a three-phase connection must be dispensed with, if possible. Increasing the maximum current output by an electrosurgical HF generator and the maximum HF voltage is therefore only possible if the efficiency level of the electrosurgical HF generator is further improved.

SUMMARY

It is an object of the embodiments disclosed herein to provide an electrosurgical HF generator, for cutting or coagulating biological tissue, having an improved efficiency level.

This object is achieved with an electrosurgical HF generator that has a power supply for supplying a generator stage, which excites an HF oscillation in an output filter comprising a parallel resonant circuit and a series resonant circuit coupled thereto. The series resonant circuit has a resonance frequency that is higher than the resonance frequency of the parallel resonant circuit.

According to the prior art, the resonance frequencies of the series resonant circuit and the parallel resonant circuit are exactly identical; otherwise, the voltage and the current do not oscillate in phase. It is an important feature of the disclosed embodiments to deviate from this teaching and to set the resonance frequency of the series resonant circuit higher than the resonance frequency of the parallel resonant circuit. This is based on recognizing that the resonance frequency of the parallel resonance circuit of the output filter is shifted to higher frequencies under load (that is, the current and the voltage are not in phase under load). Therefore, the efficiency level of an electrosurgical HF generator according to the prior art falls off with increasing load. The selection of the resonance frequencies according to the disclosed embodiments of the invention has the result that, during free-running of the electrosurgical HF generator, the voltage and the current are not in phase, although the difference between the two phases under load is reduced compared with the prior art; i.e., the efficiency level of the HF generator improves under load.

Preferably, the resonance frequency of the series resonant circuit lies in the range of 5% to 25%, preferably 7.5% to 12%, above the resonance frequency of the parallel resonant circuit. It was unexpectedly discovered that, with this choice of resonance frequencies, a particularly high level of efficiency is achieved under a typical load.

The resonance frequency of the series resonant circuit is preferably lower than the frequency of the HF oscillation produced by the electrosurgical HF generator occurring during a short-circuit of the electrosurgical HF generator. Preferably, the resonance frequency of the series resonant circuit is lower than 0.9 times, preferably lower than 0.8 times, the frequency of the HF signal occurring during a short-circuit of the electrosurgical HF generator. Accordingly, a short-circuit-proof output filter can be achieved.

Preferably, the parallel resonant circuit is coupled to the series resonant circuit via a transformer. The two resonant circuits are thereby galvanically separated from one another. A patient being treated with the electrosurgical HF generator is accordingly also galvanically separated from the power supply.

A particularly simple design of the output filter is achieved if the inductance of the parallel resonant circuit is an inductance of the transformer such as, for example, the inductance of the primary winding thereof.

Preferably, the series resonant circuit has an inductance on each side of the transformer (i.e., on each side of the secondary winding thereof). Connected on the output side of each inductance is a capacitance, with each capacitance being connected to a respective electrode.

It is advantageous if the generator stage comprises a switching stage for exciting the oscillation in the output filter, since the excitation frequency of a switching stage is simple to regulate.

The generator stage can have a control input that is coupled to the parallel resonant circuit, via a capacitor, to generate a drive signal matched to the frequency of the electrosurgical HF generator. The signal decoupled from the parallel resonant circuit, via the capacitor, can be fed to a phase shifter to which a pulse-shaping stage is connected on the output side thereof.

Using a switch to be actuated by a surgeon, such as e.g., a hand or foot switch, the signal of the pulse-shaping stage can be fed to a driver stage.

BRIEF DESCRIPTION OF THE DRAWINGS

Embodiments of the invention will now be described with reference to the drawings, in which.

DETAILED DESCRIPTION

Figure 1:
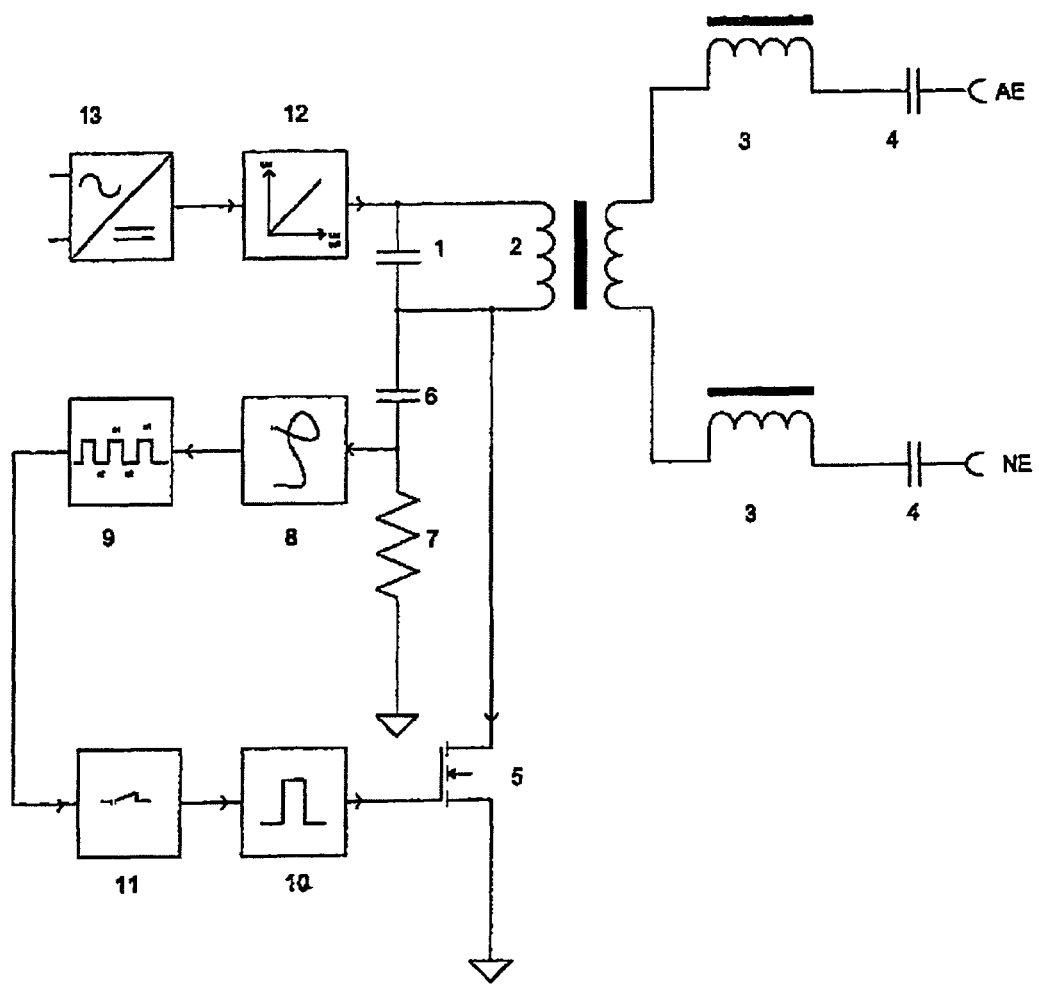
FIG. 1 is a circuit diagram showing the principle of an electrosurgical HF generator.

The electrosurgical HF generator in FIG. 1 is supplied via a main input stage 13. The input stage 13 feeds a regulated power supply unit 12, which is connected to a parallel resonant circuit comprising a capacitance 1 and an inductance 2. The inductance 2 is the primary winding of a transformer. The transformer couples the parallel resonant circuit 1, 2 to a series resonant circuit. The series resonant circuit comprises a series circuit choke 3 on each side of the secondary winding of the transformer, and a decoupling capacitor 4 connected to each choke 3 on the output side. A respective electrode is connected to each of the decoupling capacitors 4. The parallel resonant circuit 1, 2 and the series resonant circuit 3, 4 make up an output filter. The pulses necessary for driving the output filter are decoupled from the parallel resonant circuit 1, 2 by a capacitor 6 and a resistor 7. The signal from the parallel resonant circuit 1, 2 is tapped off between the capacitor 6 and the resistor 7 and fed to a phase-shifter 8. A pulse-shaping stage 9 is connected on the output side of the phase shifter 8. The phase-shifter 8 and the pulse-shaping stage 9 produce a drive signal that is synchronized to the existing resonance of the output filter and fed to a driver stage 10 via an operating unit 11. The operating unit 11 can be e.g., a hand switch or a foot switch operated by a surgeon for actuating the electrosurgical HF generator. The driver stage 10 controls a switch 5 implemented as a MOSFET, which connects the parallel resonant circuit 1, 2 to the regulated power supply unit 12.

Figure 2:
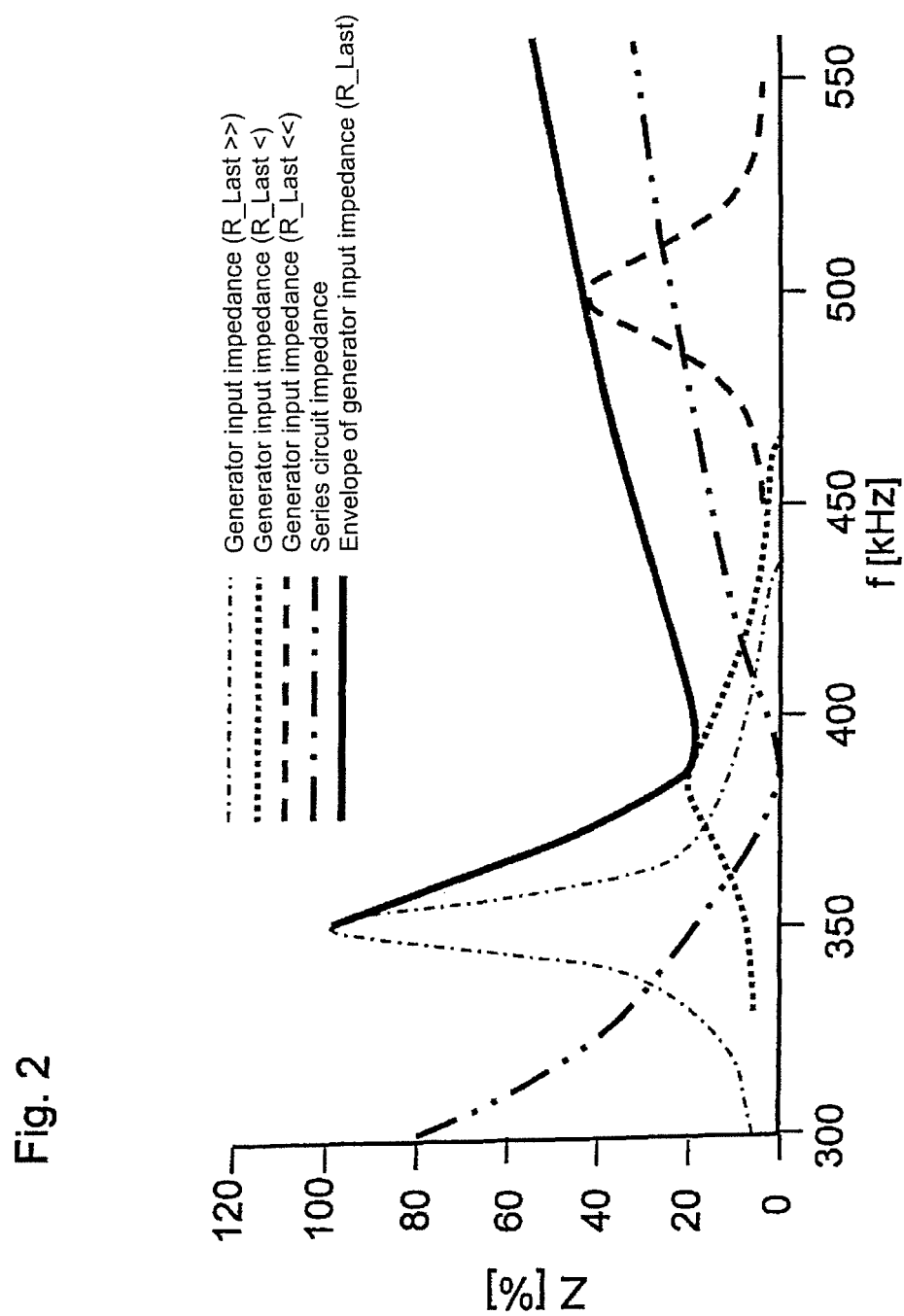
FIG. 2 shows the generator input impedance and the series circuit impedance of the electrosurgical HF generator as a function of the frequency of the HF signal.

The series circuit chokes 3 and the decoupling capacitors 4 are dimensioned such that the resonance frequency of the series resonant circuit 3, 4 is higher than the resonance frequency of the parallel resonant circuit 1, 2. For example, the generator's fundamental frequency can be selected to be equal to the parallel resonant circuit resonance frequency e.g., 350 kHz. The resonance frequency of the series resonant circuit can be e.g., 1.1 times the resonance frequency of the parallel resonant circuit, specifically 385 kHz (see FIG. 2). The generator short-circuit frequency is 500 kHz and is therefore significantly above the series circuit resonance frequency. In FIG. 2, the dot-dashed lines show the impedance of the parallel resonant circuit 1, 2 under different load conditions. The continuous line is the envelope curve. In the free running state of the electrosurgical HF generator (load impedance R_Last very high, indicated as R_Last>>) the impedance is a maximum at the fundamental frequency of 350 kHz. With increasing load, i.e., decreasing load impedance (R_Last<), the maximum shifts toward higher frequencies (e.g., to 385 kHz). The impedance of the series resonant circuit 3, 4 is a minimum at this frequency (385 kHz). Therefore, at a working frequency of 385 kHz, the voltage and current are in phase; i.e., the efficiency is optimized at the load corresponding to this frequency. Under a short-circuit (R_Last<<), the maximum of the parallel resonant circuit impedance is at the short-circuit frequency of 500 kHz.

The invention claimed is:

1. An electrosurgical high frequency (HF) generator for cutting and/or coagulating biological tissue, said generator comprising:
    a power supply; and
    a generator stage for exciting an HF oscillation signal in an output filter comprising a parallel resonant circuit coupled to a series resonant circuit, to which at least one two electrodes is are connected,
    wherein the series resonant circuit has a resonance frequency that is higher than a resonance frequency of the parallel resonant circuit, and
    wherein the resonance frequency of the series resonant circuit is lower than a frequency of the HF signal occurring during a short-circuit of the at least two electrodes.

2. The electrosurgical HF generator of claim 1, wherein the resonance frequency of the series resonant circuit is in the range of 5% to 25% above the resonance frequency of the parallel resonant circuit.

3. The electrosurgical HF generator of claim 2, wherein the resonance frequency of the series resonant circuit is in the range of 7.5% to 12.5% above the resonance frequency of the parallel resonant circuit.

4. The electrosurgical HF generator of claim 1, wherein the resonance frequency of the series resonant circuit is lower than 0.9 times the frequency of the HF signal occurring during the short-circuit of the at least two electrodes.

5. The electrosurgical HF generator of claim 4, wherein the resonance frequency of the series resonant circuit is lower than 0.8 times the frequency of the HF signal occurring during the short-circuit of the at least two electrodes.

6. The electrosurgical HF generator of claim 1, wherein the parallel resonant circuit is coupled to the series resonant circuit via a transformer.

7. The electrosurgical HF generator of claim 6, wherein the parallel resonant circuit has an inductance, which is part of the transformer.

8. The electrosurgical HF generator of claim 7, wherein the series resonant circuit has an inductance on each side of a secondary winding of the transformer.

9. The electrosurgical HF generator of claim 8, wherein a capacitance is connected to an output side of each inductance, and is also connected to one of the at least two electrodes.

10. The electrosurgical HF generator of claim 6, wherein the series resonant circuit has an inductance on each side of a secondary winding of the transformer.

11. The electrosurgical HF generator of claim 10, wherein a capacitance is connected to an output side of each inductance, and is also connected to one of the at least two electrodes.

12. The electrosurgical HF generator of claim 1, wherein the generator stage comprises a switching stage.

13. The electrosurgical HF generator of claim 1, wherein the generator stage has a control input that is coupled to the parallel resonant circuit via a capacitor.

14. The electrosurgical HF generator of claim 13, wherein a phase-shifter, with a pulse-shaping stage connected thereto on the output side thereof, is connected to the control input in order to generate a drive signal synchronized to the frequency of the HF generator.

15. The electrosurgical HF generator of claim 14, wherein the output signals from the pulse-shaping stage are fed to a driver stage via an operating unit.

* * * * *